United States Patent [19]
Gaertner

[11] 3,933,946
[45] Jan. 20, 1976

[54] N-HYDROXY-N-PHOSPHONOMETHYL-GLYCINATES

[75] Inventor: Van Russell Gaertner, Ballwin, Mo.

[73] Assignee: Monsanto Company, St. Louis, Mo.

[22] Filed: Nov. 19, 1974

[21] Appl. No.: 525,269

[52] U.S. Cl. .................. 260/944; 71/76; 71/86; 260/968
[51] Int. Cl.$^2$ .................. C07F 9/32; A01N 9/36
[58] Field of Search .................. 260/944

[56] References Cited
OTHER PUBLICATIONS
Smith, "The Chemistry of Open-Chain Organic Nitrogen Compounds," W. A. Benjamin Inc., New York, Vol. I, pp. 47, 48 (1965), Vol. II, p. 18, (1966).

*Primary Examiner*—Anton H. Sutto
*Attorney, Agent, or Firm*—Arnold H. Cole; Donald W. Peterson

[57] ABSTRACT

This disclosure relates to certain novel triesters of N-hydroxy-N-phosphonomethylglycine which are useful as herbicides for undesired plants and as growth regulators for desired plants.

3 Claims, No Drawings

N-HYDROXY-N-PHOSPHONOMETHYLGLYCINATES

This invention relates to a new class of organic chemical compounds. More particularly, this invention is concerned with a limited group of novel esters of N-hydroxy-N-phosphonomethylglycine. The specific derivatives herein are those wherein the methyl glycinate is also esterified at the phosphonic acid end of the molecule. This class of compounds has been found to display useful herbicidal activity when applied to certain varieties of weeds or undesired plants. Such compounds further display non-lethal, growth-regulating properties when applied to certain desired crop plants.

The compounds of the present invention may be represented by the structural formula

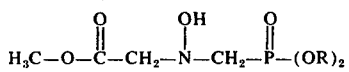

wherein R represents methyl or allyl. These novel compounds are prepared by reacting the appropriate triester of N-phosphonomethylglycine with peracetic acid as illustrated in the following examples.

PREPARATION I

A 6.3 gm. (0.03 mole) portion of trimethyl N-phosphonomethylglycinate is stirred at 20°C. in a water bath, and 4.8 gm. (0.0315 mole) of 40% peracetic acid in acetic acid is slowly added dropwise. The stirring is continued overnight. The mixture is then transferred to a beaker containing a magnetic stirring bar. The beaker is placed in the bottom of a large vacuum dessicator and is surrounded with commercial pellets of potassium hydroxide. The liquid is stirred magnetically and cautiously evacuated to <1 mm. Stirring is again continued overnight to remove volatiles including unconverted peroxides.

The resultant amber oil is distilled in a wiped-wall molecular still at 146°–160°C. (wall temperature) and 2.5–4.5$\mu$. The product obtained is trimethyl N-hydroxy-N-phosphonomethylglycinate, $n_D^{22}$ 1.4606. Elemental analysis gives 33.05% carbon and 6.07% hydrogen as against calculated values of 31.73% and 6.21% respectively for $C_6H_{14}NO_6P$.

PREPARATION II

A 26.3 gm. portion of methyl N-(diallyloxyphosphinylmethyl)glycinate is stirred at 15°–20°C. in a water bath, and 15.1 gm. of 40% peracetic acid in acetic acid is added dropwise over a 3-hour period. The mixture is stirred overnight. A starch-potassium iodide test for peroxide is positive, and a small amount of rhodium-on-alumina catalyst is added to destroy the peroxide. After 4 hours of further stirring, the mixture is then stirred magnetically and evacuated to <1 mm. in a vacuum dessicator over potassium hydroxide pellets to remove volatiles.

Distillation in a wiped-wall molecular still at 125°–140°C. (wall temperature) and 5–7$\mu$ yields methyl N-hydroxy-N-(diallyloxyphosphinylmethyl)glycinate, $n_D^{22}$ 1.4730, as a viscous yellow oil. Elemental analysis gives 41.02% carbon, 6.40% hydrogen and 12.17% phosphorus as against calculated values of 43.0%, 6.50% and 11.1% respectively for $C_{10}H_{18}NO_6P$.

The post-emergent or contact herbicidal activity of the compounds of this invention is demonstrated by means of greenhouse testing. A good grade of top soil is placed in aluminum pans and compacted to a depth of ⅜ to ½ inch (.95 to 1.27 cm.) from the top of the pan. A pre-determined number of seeds of each of several broadleaf and grassy plant species are placed on top of the soil in the pans. The seeds are covered with soil and the pans leveled. The pans are then placed on a sand bench in the greenhouse and watered from below as needed. After the plants are the desired age, each pan of plants is sprayed with a given volume of a 0.2% concentration solution of the candidate chemical, corresponding to application rates recited below. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil-ethylene oxide condensate having about 6 moles of ethylene oxide per mole of tall oil. The injuries to the plants are then observed approximately 14 days later and the results are recorded.

The spectrum of plants employed in this test included six broadleaf species and five grass species. Identification of individual species will be noted in the results which follow. At a rate of 4 lbs./acre (4.48 kg./hectare), Compound I caused 26–49% kill on morning glory and barnyard grass, but was not effective against any of the remaining species in this test. Using the same compound at a rate of 20 lbs./acre (22.4 kg./hectare) caused a kill of 26–49% on Canada thistle, cocklebur, morning glory, lambsquarters, johnson grass and downy brome, while the kill on barnyard grass increased to 50–74%. At the latter rate, additional observations of the plants were made four weeks after treatment. No change in results was noted for Canada thistle, cocklebur, morning glory and downy brome. The kill on lambsquarters and johnson grass increased to 50–74% and on barnyard grass to 75–99%. Further, 26–49% kill was noted on nutsedge and 50–74% kill was noted on quackgrass. The only two plant species on which this latter test was ineffective were velvet leaf and smartweed.

Using Compound II at a rate of 4 lbs./acre (4.48 kg./hectare), no effect was noted on lambsquarters. This compound caused 50–74% kill on morning glory and quackgrass and 75–99% kill on barnyard grass. All of the remaining species showed 26–49% kill. The plants treated at this 4 lbs./acre (4.48 kg./hectare) rate were again observed four weeks after treatment at which time 26–49% kill was noted on lambsquarters. Six of the other plant species showed an increase in the percent kill, while the remaining four species stayed at the same level of activity.

The non-lethal growth regulating activity of the compounds of this invention is also demonstrated by means of greenhouse testing. Since this type of activity is only sought after on desired crop plants, the tests were conducted on corn, a representative cereal grain and on soybeans, a representative legume.

A number of corn plants of the Pioneer 3567 variety are grown from seeds in an aluminum pan for a period of one week. The height of each corn plant is then measured to the top of the whorl. A 1% solution of each compound of the invention in acetone is prepared, and a 2.0 ml. portion of each solution is mixed with 0.8 ml. of acetone and 2.8 ml. of a water mixture with 0.05% of Aerosol OT. The resultant solution is then sprayed over the plants in the pan at an application rate equivalent to about 6.0 lbs./acre (6.72 kg./hectare). A control pan, planted at the same time as the test pan, also has its plants measured, but receives no chemical application. The pans are transferred to a greenhouse and watered from below in a sand bench. Each pan is fertilized with 40 ml. of a 1.5% solution of Rapid-Gro about 2 days after treatment.

Two weeks after treatment the height of each plant in the pans is again measured to the top of the whorl. After determining the average height increase of the plants in the untreated control pan, it is found that at least two-thirds of the corn plants treated with each compound of this invention show 26% or more stature reduction by direct comparison.

A number of soybean plants of the Wayne variety are grown from seeds in an aluminum pan for a period of one week. The height of each soybean plant is then measured to the top of the terminal bud. A solution of each compound of the invention is prepared and applied to the soybean plants in the same manner as described in the corn test. An untreated control pan is also prepared, and both pans are thereafter handled as described in said corn test.

Two weeks after treatment the height of each plant in the pans is again measured to the top of the terminal bud. After determining the average height increase of the plants in the untreated control pan, it is found that at least two-thirds of the soybean plants treated with each compound of this invention show 26% or more stature reduction by direct comparison.

While the invention has been described herein with regard to certain representative examples for the purpose of illustrating its practice, it is not to be construed as limited thereto. Those skilled in the art will readily recognize the variations and modifications which can be made without departing from the spirit and scope of the invention.

What is claimed is:
1. A compound of the formula

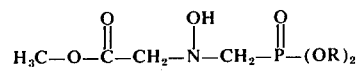

wherein R represents methyl or allyl.
2. A compound as defined in claim 1 wherein R is methyl.
3. A compound as defined in claim 1 wherein R is allyl.

* * * * *